United States Patent
Richter et al.

(10) Patent No.: US 11,964,138 B2
(45) Date of Patent: Apr. 23, 2024

(54) SUPPLEMENTARY DEVICE FOR AN INJECTION DEVICE

(71) Applicant: Sanofi-Aventis Deutschland GMBH, Frankfurt am Main (DE)

(72) Inventors: René Richter, Dresden (DE); Robert Witt, Dresden (DE); Richard Guenther, Dresden (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1010 days.

(21) Appl. No.: 16/345,942

(22) PCT Filed: Oct. 30, 2017

(86) PCT No.: PCT/EP2017/077768
§ 371 (c)(1),
(2) Date: Apr. 29, 2019

(87) PCT Pub. No.: WO2018/083061
PCT Pub. Date: May 11, 2018

(65) Prior Publication Data
US 2019/0262544 A1    Aug. 29, 2019

(30) Foreign Application Priority Data
Nov. 1, 2016 (EP) ..................... 16196678

(51) Int. Cl.
*A61M 5/315* (2006.01)
*A61M 5/178* (2006.01)
*A61M 5/31* (2006.01)

(52) U.S. Cl.
CPC ........ *A61M 5/31535* (2013.01); *A61M 5/178* (2013.01); *A61M 5/3155* (2013.01);
(Continued)

(58) Field of Classification Search
CPC .............. A61M 5/31535; A61M 5/178; A61M 5/3155; A61M 2005/3126;
(Continued)

(56) References Cited

U.S. PATENT DOCUMENTS 5,971,963 A    10/1999  Choi
9,782,543 B2   10/2017  Groeschke et al.
(Continued)

FOREIGN PATENT DOCUMENTS

CN    101438327    5/2009
CN    102695535    9/2012
(Continued)

OTHER PUBLICATIONS

International Preliminary Report on Patentability in Application No. PCT/EP2017/077768, dated May 7, 2019. 6 pages.
(Continued)

*Primary Examiner* — Lauren P Farrar
(74) *Attorney, Agent, or Firm* — Fish & Richardson P.C.

(57) ABSTRACT

In one aspect the present disclosure refers to a supplementary device for a manually operable injection device, the supplementary device comprising:
a body attachable to an elongated housing of the injection device,
at least one connector connected to the body and connectable to the housing, wherein the body is attachable to the housing via the at least one connector,
a sensor arrangement coupled to at least one of the body and the at least one connector and configured to measure a longitudinal force component acting between the at least one connector and the body in a direction parallel to the elongation of the housing.

17 Claims, 3 Drawing Sheets

(52) U.S. Cl.
CPC ............... *A61M 2005/3126* (2013.01); *A61M 2205/332* (2013.01); *A61M 2205/3327* (2013.01); *A61M 2205/3331* (2013.01); *A61M 2205/3375* (2013.01); *A61M 2205/43* (2013.01); *A61M 2205/50* (2013.01); *A61M 2205/52* (2013.01); *A61M 2205/586* (2013.01); *A61M 2205/70* (2013.01); *A61M 2205/8206* (2013.01)

(58) Field of Classification Search
CPC .... A61M 2205/332; A61M 2205/3327; A61M 2205/3331; A61M 2205/3375; A61M 2205/43; A61M 2205/50; A61M 2205/52; A61M 2205/586; A61M 2205/70; A61M 2205/8206
See application file for complete search history.

(56) References Cited

U.S. PATENT DOCUMENTS

| | | | |
|---|---|---|---|
| 10,195,355 B2 * | 2/2019 | Allerdings | ........ A61M 5/31535 |
| 10,446,269 B2 | 10/2019 | Groeschke et al. | |
| 2004/0133166 A1 * | 7/2004 | Moberg | .............. A61M 5/1456 |
| | | | 604/151 |
| 2004/0207385 A1 | 10/2004 | Gafner et al. | |
| 2014/0005950 A1 * | 1/2014 | Groeschke | .............. G16Z 99/00 |
| | | | 702/19 |
| 2014/0012226 A1 | 1/2014 | Hochman | |
| 2016/0213851 A1 | 7/2016 | Weibel et al. | |

FOREIGN PATENT DOCUMENTS

| | | | |
|---|---|---|---|
| CN | 104755118 | 7/2015 | |
| CN | 105816943 | 8/2016 | |
| CN | 105854130 | 8/2016 | |
| EP | 2190506 | 6/2010 | |
| GB | 2478085 | 10/2011 | |
| JP | 2009-050709 | 3/2009 | |
| JP | 2014-516599 | 7/2014 | |
| JP | 2014-520617 | 8/2014 | |
| JP | 2015-506771 | 3/2015 | |
| JP | 2016-515453 | 5/2016 | |
| WO | WO 2004/078239 | 9/2004 | |
| WO | WO 2004/078240 | 9/2004 | |
| WO | WO 2004/078241 | 9/2004 | |
| WO | WO 2009/024562 | 2/2009 | |
| WO | WO-2009024562 A1 * | 2/2009 | .......... A61M 5/1452 |
| WO | WO 2011/083377 | 7/2011 | |
| WO | WO 2011/124780 | 7/2012 | |
| WO | WO 2012/117255 | 9/2012 | |
| WO | WO 2012/127046 | 9/2012 | |
| WO | WO 2013/010893 | 1/2013 | |
| WO | WO 2013/120778 | 8/2013 | |
| WO | WO 2014/064691 | 5/2014 | |
| WO | WO 2014/067879 | 5/2014 | |
| WO | WO 2014/173773 | 10/2014 | |
| WO | WO 2016/005421 | 1/2016 | |
| WO | WO 2016/118736 | 7/2016 | |
| WO | WO 2016/140853 | 9/2016 | |
| WO | WO 2016/161346 | 10/2016 | |
| WO | WO 2016/162298 | 10/2016 | |

OTHER PUBLICATIONS

International Search Report and Written Opinion in Application No. PCT/EP2017/077768, dated Feb. 13, 2018, 8 pages.

* cited by examiner

SUPPLEMENTARY DEVICE FOR AN INJECTION DEVICE

CROSS REFERENCE TO RELATED APPLICATIONS

The present application is the national stage entry of International Patent Application No. PCT/EP2017/077768, filed on Oct. 30, 2017, and claims priority to Application No. EP 16196678.3, filed on Nov. 1, 2016, the disclosures of which are incorporated herein by reference.

TECHNICAL FIELD

The present disclosure relates to an apparatus for supplementing a medical device configured to eject or to inject a medicament. In particular, the present disclosure relates to a supplementary device for a manually operable injection device and further relates to a kit comprising a supplementary device and an injection device. The disclosure also relates to a method of monitoring the operation of a manually operable drug delivery device or injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day.

For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dose dial and observing the actual dose from a dose window or display of the insulin pen. The dose is then injected by inserting the needle into a suited skin portion and pressing an injection button or dose button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 A1 discloses a medical device with a value sensor. There, a Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The medical delivery device as described in WO 2009/024562 A1 comprises a control circuitry and a sensor system wherein the sensor system comprises a force sensor and whereby a pressure in the fluid drug or the force acting on the drug via an actuator can be monitored. Monitoring of the pressure in the fluid drug requires vast modifications to the medical delivery device. Such modifications are rather cost intensive to develop and are also unattractive, especially for injection devices that are configured and designed as so-called disposable devices.

It is therefore desirable to provide a supplementary device for a manually operable injection device that provides a rather simple, cost-efficient, intuitive approach to monitor operation of the injection device. The supplementary device should provide and enable monitoring of the operation and handling of the injection device without the necessity to modify the structure or operation of the injection device. The supplementary device should be combinable with a variety of injection devices that are commercially available. It is a further aim to provide a new, improved and rather robust and failure safe method of monitoring the operation of a manually operable injection device.

SUMMARY

In one aspect a supplementary device for a manually operable injection device is provided. The supplementary device comprises a body attachable to an elongated housing of the injection device. The supplementary device further comprises at least one connector that is connected to the body and which is connectable to the housing. The body of the supplementary device is attachable to the housing of the injection device via the at least one connector. The body is attachable to an outside facing portion of the housing, via the at least one connector. The supplementary device further comprises a sensor arrangement that is coupled to at least one of the body and the at least one sensor.

The sensor arrangement is configured to measure a longitudinal force component acting between the at least one connector and the body in a direction parallel to the elongation of the housing and/or parallel to the elongation of the body. When connected and attached to the housing of the injection device the at least one connector of the supplementary device is fixedly attached to the housing. Any longitudinal force acting between the connector and the body is detectable and measurable by the sensor arrangement. When the at least one connector is fixedly attached to the housing any longitudinal force effect acting between the body and the housing is measurable by the sensor arrangement.

The entire supplementary device, i.e. the body, the at least one connector and the sensor arrangement are arranged outside the housing of the injection device when attached to the housing of the injection device. In this way the supplementary device is configured to engage with a manually operable injection device without the necessity to make any modifications to the injection device. Since the sensor arrangement is configured to measure a longitudinal force component acting between the at least one connector and the body and since the at least one connector is connectable exclusively to the elongated housing of the injection device the supplementary device is particularly configured to measure a counter force induced by a dispensing force applied to a dose button, e.g. located at a proximal end of the injection device.

A longitudinal force component measurable by the sensor arrangement is typically indicative or identical to a counter force that has to be provided, e.g. by a hand of a user holding the injection device during a manually operated injection procedure. Measuring of the longitudinal force component and hence of a counter force is beneficial in that the injection device does not have to be manipulated or modified in order to implement a monitoring function of the supplementary device.

In an embodiment the body of the supplementary device forms a handhold with an outer surface that is configured to be gripped by a palm of a hand of a user. By forming a handhold the supplementary device connected to the housing of the injection device provides a gripping means by way of which the injection device is supported and gripped in a hand of a user. Typically, the injection device comprises a dose button at its proximal end that is to be depressed by a finger of the user, e.g. by a thumb of that hand of the user that encloses or holds the body of the supplementary device.

In other words, the body of the supplementary device is connectable and attachable to an outer circumference of the housing of the injection device so as to provide a handhold for gripping, supporting and holding the supplementary device at least during the process of injection of a liquid medicament.

In a further embodiment the body of the supplementary device comprises a hollow sleeve with an inner diameter that is larger than an outer diameter of the housing of the injection device. The inner diameter of the hollow sleeve is larger than the outer diameter of at least a portion of the housing of the injection device, which housing portion is configured to be enclosed by the hollow sleeve. Since an inner diameter of the hollow sleeve is larger than an outer diameter of the housing the housing of the injection device is insertable into the hollow sleeve. This enables a rather intuitive, easy and quick mutual assembly of the body of the supplementary device and the housing of the injection device. In other words, the body of the supplementary device may be simply slipped over the outer circumference of the housing of the injection device.

Typically, the body is releasably connectable and releasably fixable to the housing of the injection device. This is of particular benefit when the injection device is configured as a disposable injection device that is intended to be discarded in its entirety once the medicament provided therein has been used up or should no longer be used. Prior to disposal of the injection device the supplementary device and the injection device are disconnectable. Here, the at least one connector is detachable from the outer circumference of the housing of the injection device so as to separate the body and the housing from each other. When the injection device has been subject to discarding, a new or another injection device for subsequent use is attachable and connectable to the body and hence to the at least one connector. In this way, the supplementary device is usable with a variety and with multiple, e.g. disposable manually operable injection devices. Due to its releasable engagement with the injection device the supplementary device is inherently configured to monitor and/or to capture a dosing and injection history conducted by multiple injection devices.

In a further embodiment the at least one connector is attached to an inner side of a sidewall of the hollow sleeve. The hollow sleeve may be of cylindrical or tubular shape. Having the connector attached to an inner side of a sidewall of the hollow sleeve allows for an assembly configuration with the injection device in which the at least one connector is sandwiched between the inner side of the sidewall of the hollow sleeve and an outside facing portion of the housing of the injection device. If the hollow sleeve and the housing are of substantially cylindrical or tubular shape the at least one connector is radially squeezed between the sidewall of the hollow sleeve and the outer circumference of the housing of the injection device.

Mutual attachment, connection and fixing of the at least one connector and the housing may include a positive engagement or a non-positive engagement. The housing and the at least one connector may comprise mutually corresponding positively engaging fastening members, such as snap features, radial protrusions and corresponding radial recesses. Alternatively, the at least one connector and the housing may be fixable relative to each other by way of friction. The at least one connector and the housing may be force fitted or press fitted. At least one of the housing, the at least one connector and the body may comprise a somewhat elastically deformable structure that enables a mutual press fit, friction fit or force fit between the at least one connector and the housing.

Typically, the housing and/or the body are made of a thermoplastic material, such as an injection moldable thermoplastic material. Also, the at least one connector may comprise or may consist of a thermoplastic material that enables a mutual clamping of the body and the housing. Alternatively or additionally, the at least one connector may comprise an elastomeric material, such as natural or synthetic rubber by way of which a rather easy, durable and reliable clamping, press fitting or force fitting of the housing and the body can be obtained.

The at least one connector may for instance comprise an annular shape or ring-like shape along the inner circumference of the sidewall of the hollow sleeve. With a correspondingly-shaped tubular or cylindrical housing a clamping force that is rather homogeneous along the outer circumference of the housing or along the inner circumference of the body or the connector can be obtained. Such a configuration is beneficial for a reliable, durable and mechanically stable mutual connection of body and housing.

According to another embodiment the body is shaped to enclose at least a portion of the elongated housing. By enclosing at least a portion of the elongated housing, typically by enclosing a proximal portion of the tubular-shaped elongated housing of the injection device a rather simple and intuitive mutual fastening of body and housing can be provided. Assuming a cylindrical shape of both, the body and the elongated housing it is even conceivable to arrange the body in an arbitrary angular position with regard to the elongated housing. The tubular shape of the body or of its hollow sleeve and a corresponding tubular shape of the elongated housing enables a rotation-invariant attachment of the body to the housing. In other words, the body and the housing can be mutually attached and mutually fixed to each other at any given arbitrary angular orientation of the body relative to the housing with longitudinal axis of the body as an axis of rotation. When attached to the housing a longitudinal and central axis of the body typically coincides or at least extends parallel to a longitudinal and centrally located axis of the housing of the injection device.

In one embodiment the sensor arrangement is integrated into at least one of the at least one connector and the body. The sensor arrangement may be integrated into only one of the body and the at least one connector. The sensor arrangement may be exclusively integrated into the body. Then, the sensor arrangement will be coupled and/or connected to the at least one connector. In other embodiments the sensor arrangement is exclusively integrated into the at least one connector. If there are provided several connectors the sensor arrangement may be distributed among various connectors and may be distributed across multiple connectors. Then, the sensor arrangement comprises multiple sensor components, each of which being integrated into one or several of the multitude of connectors. If there is only provided a single connector the entire sensor arrangement may be integrated into that particular connector. When integrated into the at least one connector the sensor arrangement is further coupled or connected to the body so as to provide a longitudinal force component measurement between the connector and the body.

It is also conceivable that the sensor arrangement is integrated into both, the at least one connector and the body. It is even conceivable, that the at least one connector and the body are connected via the sensor arrangement. In this way, any forces to be transferred between the body and the housing of the injection device will be transferred from the body to the sensor arrangement and further from the sensor arrangement to the connector and further to the housing. By integrating the sensor arrangement into at least one of the body and the at least one connector the sensor arrangement is inherently arranged in a flux of force between the body and the housing when the supplementary device is attached to the housing.

Integration of the sensor arrangement into at least one of the body and the at least one connector is also beneficial in terms of durability, mechanical stability and robustness of the supplementary device. By integrating the sensor arrangement into at least one of the body and the at least one connector the sensor arrangement is inherently protected against environmental influences. The sensor arrangement may be encapsulated inside the body and/or inside the at least one connector. In this way it is inherently protected against humidity, dust, hazardous electromagnetic radiation and/or other environmental influences that may harm the integrity, functionality or long term stability of the sensor arrangement.

In one embodiment the at least one connector comprises a lever with a first end and with a second end. The second end is located opposite to the first end. The first end is further connectable to the elongated housing and the second end is mechanically connected to the sensor arrangement. The lever may comprise an L-shaped structure. Any longitudinal force component arising during an injection procedure may be absorbed or received at the first end of the lever. This may induce either a pivoting or a deformation of the lever so that the second end thereof may transfer a respective force component to the sensor arrangement. The lever may extend through the body. It may even intersect a sidewall of the body. In particular, the first end of the lever may be located inside the body whereas the second end of the lever may reach through a sidewall of the body or may even protrude from the sidewall of the body. In this way, the lever enables arranging of the sensor arrangement to an outer circumference or to an outer section of the body. This may be beneficial for data transmission or data processing of electrical signals obtainable from the sensor arrangement.

The first and second ends of the lever may form end sections of a respective leg. Hence, the lever may comprise a first leg with the first end and a second leg with the second end. The legs may extend at a predefined angle, e.g. at about 90° with respect to each other. The first and the second leg may have a different elongation. In this way a leverage effect could be provided leading to an attenuation or amplification of a measureable longitudinal force effect.

In one embodiment the sensor arrangement comprises at least one or more of a strain gauge, a force sensor, a pressure sensor, a switch and a microphone. The sensor arrangement is typically electrically implemented so as to provide electrical signals indicative of the presence of a longitudinal force component. Depending on the specific implementation of the sensor arrangement the at least one connector and the body may either be rigidly attached to each other or the at least one connector is displaceably attached to the body so as to enable at least a mutual displacement of the at least one connector and the body for the purpose of measuring a longitudinal force component.

The strain gauge, the force sensor and/or the pressure sensor may comprise piezoelectric layers or piezoelectric components that provide a reliable and cost-efficient as well as space saving approach to measure a longitudinal force component. When the sensor arrangement is implemented as a switch it is typically provided with a compression spring that is compressible during a mutual displacement of the body with regard to the at least one connector as a longitudinal force is applied to the housing of the injection device when the supplementary device is attached thereto. When the level of the longitudinal force component applied to the housing exceeds a predefined threshold the switch may provide an electric contact or may interrupt an electric contact previously provided. Establishing of the electric contact or disruption of an electric contact is then a measurable indication that a predefined level of the longitudinal force component has been reached.

In one embodiment the supplementary device further comprises a processor or a controller electrically connected to the sensor arrangement. The processor is configured to process and/or to record or to capture signals obtainable from the sensor arrangement. The processor may be either configured to directly process electrical signals obtained from the sensor arrangement during use of the injection device with the supplementary device attached thereto. Alternatively, the processor may simply capture and record electrical signals obtained from the sensor arrangement during use of the injection device. In this case the supplementary device is further equipped with a storage or memory as well as with an interface so as to enable a readout of the storage and to enable signal- and data processing with some other electronic device connectable to the supplementary device in a data transmitting way.

When configured to directly process electric signals from the sensor arrangement the processor may extract information or data from the electric signals of the sensor arrangement that are indicative of e.g. a time at which an injection took place, a duration of an injection procedure, a size of a dose of the medicament actually injected during the injection procedure and/or a hold time the injection needle was left inside biological tissue after the injection procedure terminated or after the injection was completed.

Furthermore, the processor may also monitor and capture the magnitude of a dispensing force applied by a person to the manually operable injection device. Also, a pressure pattern over time or a pressure profile may be monitored and/or stored.

In one embodiment the sensor arrangement is also configured to measure the longitudinal force component quantitatively. Hence, the sensor arrangement is configured to measure the magnitude of the longitudinal force component exerted to the housing relative to the body of the supplementary device. In this way the sensor arrangement may distinguish between rather low longitudinal force components and rather high longitudinal force components. A rather high longitudinal force component above a predefined threshold is an indication that a dispensing procedure has been triggered or is actually taking place. By measuring and capturing as well as monitoring a force profile or pressure profile by means of the sensor arrangement the start and a termination of a dispensing procedure can be precisely detected. From this, a duration of a dispensing procedure can be determined, simply by subtracting a time at which injection terminated and a time at which injection started.

Furthermore, monitoring, especially long term monitoring of force profiles or pressure profiles arising during use and during injection of the medicament may be evaluated in order to characterize a user's habits or usage of the injection device.

In one embodiment the sensor arrangement comprises a microphone and at least one of a strain gauge, a force sensor, a pressure sensor and a switch. Furthermore, the processor is configured to start processing or recording of signals from the sensor arrangement when a magnitude of the longitudinal force component is above a predefined threshold. Recording or processing of signals may include counting of acoustic signals generated by the injection device during dose dispensing and hence during an injection procedure. With some commercially available manually operable injection devices, such as with a large variety of pen-type injectors setting as well as dispensing of a dose of a medicament is accompanied by regular or recurrent click sounds that are generated by a click sound generator of the injection device. Each click sound is indicative of the setting and/or dispensing of a discrete quantity of the medicament.

In order to characterize and to monitor dose dispensing or an injection procedure the supplementary device must be enabled to distinguish between a dose setting action and a dose dispensing action. Typically, longitudinal force components measurable by the sensor arrangement when the supplementary device is attached to the injection device only arise during a manually operated injection procedure or dose dispensing procedure. In this way, the at least one of the strain gauge, the force sensor, the pressure sensor and the switch may be used and configured to detect the start and the termination of a dispensing procedure. The microphone of the sensor arrangement is then configured to detect recurrent click sounds during the injection procedure so as to gain information about the size of a dose actually dispensed or injected.

Measuring of the longitudinal force component of the sensor arrangement can be hence used for activating and/or deactivating of the microphone to count recurrent click sounds during dose dispensing.

In another aspect a kit is provided that comprises a supplementary device as described above. The kit further comprises a manually operable injection device. The injection device comprises an elongated housing with a distal end and with a proximal end and with a dose button located at the proximal end. The dose button is depressible towards the distal end, hence in a distal direction to initiate and/or to conduct dispensing of a dose of a medicament. The manually operable injection device is characterized in that a dispensing force for expelling the medicament from a cartridge is provided by the user by depressing the dose button towards the distal end. The injection device is typically void of an electrically operated drive for providing a dispensing force.

The kit can be delivered to end users with the supplementary device readily attached to the housing of the injection device or in a configuration in which the supplementary device and the injection device are provided as separate components that have to be manually attached and fixed to each other by the end user prior to start using of the injection device.

In a further embodiment the injection device is configured to accommodate a cartridge that is filled with the medicament and which is sealed towards the proximal end with a piston displaceable inside a barrel of the cartridge. The injection device further comprises a drive mechanism with a piston rod to operably engage with the piston of the cartridge for displacing the piston towards the distal end, in particular for the purpose of dispensing of a dose of the medicament for injecting the medicament into biological tissue.

For the process of injection the distal end of the cartridge and hence the distal end of the housing of the injection device is typically provided with a detachable piercing assembly, such as an injection needle. The injection needle is typically double-tipped. When mounted the injection device a proximal tip of the injection needle is in fluid connection with the interior of the cartridge and a distal tip of the injection needle is configured to pierce the skin of a patient or a person so as to deliver the liquid medicament inside the respective biological tissue.

The injection device further comprises a click sound generator that is configured to generate recurrent click sounds during a displacement of the piston rod towards the distal end. The click sound generator may be further configured to generate recurrent click sounds also during setting or dialing of a dose. Each occurrence of a click sound is indicative of a discrete size of a dose. By counting the number of recurrent click sounds the size of a dose can be calculated, e.g. by the processor of the supplementary device. The recurrent click sounds generated by the click sound generator are typically recorded and detected by the microphone of the sensor arrangement.

The microphone is selectively activatable, or signals obtainable from the permanently activated microphone are only processed and analyzed at such times where the longitudinal force component concurrently measured by the sensor arrangement is above a predefined threshold. The threshold is selected in accordance to a dispensing force normally required to initiate and to conduct a manually operated dispensing procedure with the injection device. Typically, the predefined force threshold is slightly below a force level required for initiating and/or conducting of a dispensing procedure. In this way eventual friction losses due to mechanical interaction of the drive mechanism can be compensated.

In one embodiment the supplementary device is attachable or is attached to a proximal portion of the elongated housing at a predefined distance from the proximal end. Measuring of a longitudinal force component exerted to the injection device during and for dose dispensing does not require arrangement of the sensor arrangement inside or to the dose button of the injection device. For implementing a monitoring of the operation and handling of the injection device the supplementary device can be attached to a rather arbitrary portion of the housing. It may be located at a position that is remote from the dose button and which is separated from the dose button by a predefined non-zero distance.

The arbitrary attachment of the supplementary device to the outer circumference of the housing of the injection device provides a large variety of configurations for attaching the supplementary device to the housing of the injection device. In particular, the supplementary device can be attached to a portion of the housing that is separated and remote from a window through which the actual size of a dose may be displayed during dose setting and/or during dose dispensing. In embodiments, wherein the supplementary device and e.g. its hollow sleeve may cover the dose size indicating window of the injection device it is conceivable to provide a respective recess in the sidewall of the body or to manufacture at least a portion of the body of a transparent material so that the dose size indicating window of the injection device remains visible for a user.

In another aspect a method of monitoring the operation of a manually operable injection device is provided. The method comprises the steps of attaching a supplementary device as described above to an elongated housing of the injection device and connecting at least one connector of the supplementary device to a housing of the injection device. Then, the supplementary device is grasped with the injection device attached thereto. Typically, a user that may intend to inject a dose of the medicament grasps the supplementary device with the palm of a hand. In a following step a force is exerted to a dose button that is located at a proximal end of the injection device. During or while the dose button is depressed in distal direction a longitudinal force component acting between a body of the supplementary device and the housing in a direction parallel to the elongation of the housing is measured while the force is applied to the dose button.

The force applied or applicable to the dose button during the monitoring of the operation of the manually operable injection device may be a dispensing force sufficient to depress or to displace the dose button in a distal direction so as to trigger a dispensing operation of the injection device.

The method of monitoring is typically conducted and executable by a supplementary device as described above connected to an injection device as described above. Typically, the method of monitoring is conductible by means of a kit as described above. The method of monitoring may comprise further steps, such as dialing or setting of a dose prior to exert a dispensing force to the dose button. In addition, and when equipped with both, a microphone and one of a strain gauge, a force sensor, a pressure sensor and a switch the method of monitoring the operation of the injection device may further comprise the step of counting recurrent click sounds generated by a click sound generator of the injection device while the dispensing force is applied to the dose button.

In this way and as described above the size of a dose actually dispensed or injected can be precisely determined by means of the supplementary device. Generally, the features, benefits and effects obtainable with the supplementary device and with the kit as described above equally reflect and also apply to the method of monitoring the operation of the injection device; and vice versa.

In the present context a distal end or a distal direction refers to that end of the injection device that is oriented towards a portion of a body of a person or an animal that should be subject to injection. A proximal direction or a proximal end refers to the opposite end of the injection device, which is typically opposite to the dispensing end of the injection device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as defined in the appended claims. Further, it is to be noted, that any reference numerals used in the appended claims are not to be construed as limiting the scope of the invention.

BRIEF DESCRIPTION OF THE FIGURES

In the following, embodiments of the present invention will be described by making reference to the drawings, in which.

DETAILED DESCRIPTION

Figure 1:
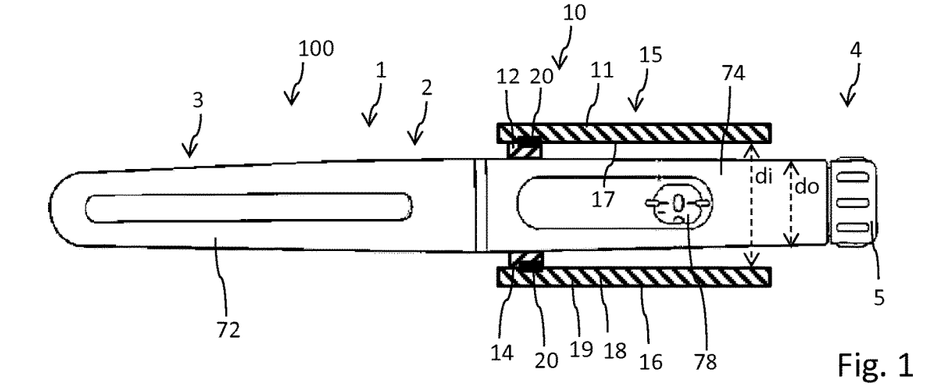
FIG. 1 schematically shows an injection device with a supplementary device attached thereto in an initial configuration.
Figure 2:
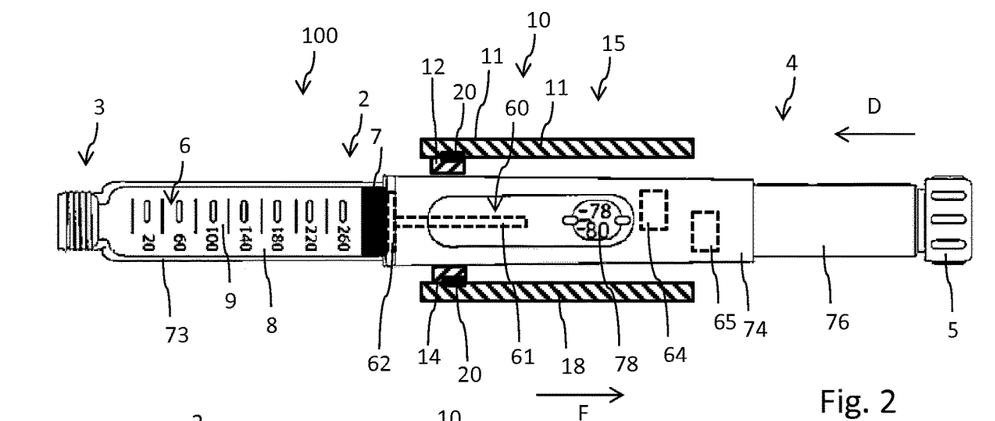
FIG. 2 shows the devices according to FIG. 1 with the injection device in a configuration in which a dose is set and in which the injection device is ready for dispensing of a dose.

FIGS. 1 and 2 are illustrative of a manually operable injection device configured as a pen-type injector for dispensing of a liquid medicament 9 located inside a cartridge 6. The injection device 1 comprises an elongated housing 2. The housing 2 comprises various housing portions, e.g. a distal housing portion 73 that provides a support for the cartridge 6 and a proximal housing component 74 which is configured to accommodate a drive mechanism 60. The cartridge 6 typically comprises a vitreous barrel 8 of cylindrical or tubular shape.

The distal housing component 73 may be also denoted as a cartridge holder having a visual scale to visually indicate the filling level of the cartridge 6 accommodated therein. It is immediately apparent from a comparison of FIGS. 1 and 2, that the distal housing component 73 can be covered by a protective cap 72 that is detachably connectable to the distal housing component 73 or to the proximal housing component 74. The protective cap 72 serves to protect the distal housing component 73 against environmental influences, e.g. when there is no injection needle attached to the distal end 3.

The barrel 8 is sealed in proximal direction by a piston 7 that is slidably displaceable along the elongation of the cartridge 6 in order to expel the medicament 9 via a double-tipped injection needle that is detachably connectable to a distal end 3 of the housing 2. The double-tipped injection needle (not illustrated) typically comprises a cup-shaped needle hub for threaded engagement with the distal end 3 of the elongated housing 2. The distal end 3 typically comprises a central through opening to receive a proximal portion of the injection needle. When mounted to the distal end 3 the proximal end of the injection needle penetrates a distally located seal, e.g. a septum of the cartridge 6 so as to obtain access to the interior space of the barrel 8.

The distal end of the injection needle is configured to penetrate and to pierce biological tissue in order to deposit a dose of the liquid medicament 9 as the piston 7 advances towards the distal end 3 of the housing 2 and hence of the cartridge 6. The piston 7 is displaceable in distal direction by means of a piston rod 61, which is indicated in FIG. 2. Typically, the piston rod 61 comprises a radially enlarged pressure piece 62 at a distal end that is configured to apply distally directed pressure to the piston 7.

The manually operable injection device 1 may be characterized in that a force for displacing the piston rod 61 in distal direction is exclusively and completely provided by a user of the device. The piston rod 61 is a component of a drive mechanism 60 housed inside the proximal housing component 74 of the housing 2 of the injection device 1. At a proximal end 4 of the housing 2 there is provided a dose button 5, which in a proximally extended configuration as shown in FIG. 2 is depressible in distal direction and hence towards the distal end 3 by the user himself. In this way, a dispensing force D is applicable to the dose button 5 in order to displace the dose button 5 from the proximally extended configuration as shown in FIG. 2 into the initial configuration in which the dose button 5 is located close to the proximal end 4 of the housing 2. As indicated in FIG. 2, the dose button 5 is provided at a proximal end of a sleeve 76 that is axially or longitudinally displaceable relative to the housing 2. The sleeve 76 may be configured as a dose indicating sleeve having a sequence of dose indicating numbers on its outer circumference that may show up in a dose indicating window 78 of the proximal housing component 74.

The dose button 5 as indicated in FIGS. 1 and 2 provides a double function. It has an annular shape with gripping features along its outer circumference. So for setting of a dose of variable or fixed size the dose button 5 is to be rotated either clockwise or counter-clockwise relative to the housing 2 in order to increase or to decrease a size of a dose during a dose setting procedure and prior to a dose dispensing or dose injection procedure.

The drive mechanism 60 typically comprises at least one or several clutches as well as some kind of a gear 65 to transfer a distally directed or rotative motion of at least one of the dose button 5 and the sleeve 76 into a distally advancing movement of the piston rod 61. The general operation and functionality of one example of a manually operable injection device is for instance known from any one of the documents WO 2004/078239 A1, WO 2004/078240 A1 and/or WO 2004/078241 A1. Such injection devices are well known in the art and are commercially distributed and need no further explanation here.

The manually operable injection device 1, in particular its drive mechanism 60 also comprises a click sound generator 64 that is configured to generate recurrent or regular audible sounds, such as click noises that are audible by a user of the device. A click sound generator 64 is configured to audibly indicate to a user, that at least a dose dispensing or dose injection procedure is currently in progress. The click sound generator 64 may be also active during dose setting so as to provide an audible feedback to a user that a discrete size of a dose has been actually dialed or set.

In FIGS. 1 and 2 there is further shown in cross-section a supplementary device 10 attached to the elongated housing 2 of the injection device 1. The supplementary device 10 comprises a body 11 with at least one connector 12, 14. As shown in FIGS. 1 and 2 the supplementary device 10 is attached to an outer circumference of the housing 2, in particular of the proximal housing component 74. The at least one connector 12, 14 provides a mechanical connection between the body 11 and the housing 2. The supplementary device 10 further comprises a sensor arrangement 20 that is coupled to at least one of the body 11 and the at least one connector 12, 14. The sensor arrangement 20 is furthermore at least configured to measure a longitudinal force component F acting between the at least one connector 12, 14 and the body 11 in a direction parallel to the elongation of the housing 2 and/or in a direction parallel to the elongation or parallel to the symmetry axis of the body 11 or of the supplementary device 10.

In the embodiment as shown in FIGS. 1 and 2 the body 11 is attached and fixed to the outer circumference of the housing 2 by means of the connector 12, 14. The connector 12, 14 may comprise various connector components or may comprise a single, e.g. annular-shaped connector 12 or 14 extending along the inner circumference of the body 11. When the at least one connector 12, 14 is fixed and attached to the outer circumference of the housing 2 any longitudinally directed forces acting between the body 11 and the housing 2 can be detected, measured and monitored by the sensor arrangement 20 and the supplementary device 10.

The body 11 of the supplementary device 10 further forms a handhold 15 with an outer surface 16 that is configured to be gripped or to be enclosed by a palm of a hand of a user. In other words, the body 11 forms a handhold to grasp and to hold the injection device 1 when the supplementary device 10 is attached to the housing 2. For dispensing of a dose a user typically applies a distally directed dispensing force D to the proximally extending dose button 5. The dispensing force D is typically applied to the dose button 5 with a thumb whereas residual fingers of the same user's hand grasp the handhold 15 and hence the outer surface 16 of the body 11 of the supplementary device.

The sensor arrangement is located in a flux of force between the body 11 and the housing 2. The sensor arrangement 20 is configured to detect and to measure a longitudinal force component F that is directed in an opposite direction compared to the dispensing force D. In other words, the longitudinal force component F substantially equals a reaction force to be provided by a user in order to displace the dose button 5 in distal direction relative to the housing 2. Apart from friction losses in the drive mechanism 60 the longitudinal force component F is substantially equal in magnitude to the dispensing force D.

As indicated in FIGS. 1 and 2 the body 11 may comprise a hollow sleeve 16 having an inner diameter di that is larger than an outer diameter do of the housing 2 of the injection device. In this way the body 11 and hence the entire supplementary device 10 can be slipped over the housing 2 of the injection device. Typically, the at least one connector 12, 14 protrudes inwardly from an inner side 17 of a sidewall 19 of the hollow sleeve 18 of the body 11. In this way, the at least one connector 12, 14 may provide a mechanical connection to the outer circumference of the housing 2. The at least one connector 12, 14 may be configured to positively engage or to frictionally engage with the housing 2. In some embodiments the dimensions and the geometries of the body 11, the at least one connector 12, 14 and the housing 2 are such, that a friction fit or a press fit can be obtained between the body 11 and the housing 2. Other embodiments may be based on mutually corresponding and complementary engaging connection members, such as positively engaging connection members that provide and enable a releasable positive engagement of the body 11 and the housing 2.

The supplementary device 10 and in particular its body 11 with the at least one connector 12, 14 attached thereto is releasably engageable with the housing 2. In this way, various injection devices 1 can be connected to the supplementary device 10 either on demand or sequentially. If the injection device 1 is intended to be discarded in its entirety the supplementary device 10 can be detached therefrom and can be connected and fixed to another, a new injection device. In this way the supplementary device 10 may provide an injection device-independent monitoring of device handling and injection procedures. The supplementary device is hence configured to capture and to log a dosing history conducted by a user.

The specific implementation and arrangement of the sensor arrangement may vary. The sensor arrangement 20 may be integrated into at least one of the connector 12, 14 and the body 11. The sensor arrangement 20 may be completely integrated or attached to the body 11. Then the sensor arrangement 20 will be connected or mechanically coupled to the connector 12, 14. In other embodiments the sensor arrangement 20 is integrated into or connected to the connector 12, 14. Then, it will be coupled to the body 11. In other embodiments the sensor arrangement 20 may be integrated or arranged in an interface section of connector 12, 14 and body 11. It may be hence integrated into both, the body 11 and the at least one sensor arrangement 12, 14.

It is also conceivable, that the connector 12, 14 is connected via the sensor arrangement 20 to the body 11. With all these embodiments the sensor arrangement 20 is located in the flux of force between a radially inwardly located end of the connector 12, 14 and a radially outwardly located handhold 15 or outer surface 16 of the body 11.

Figure 3:
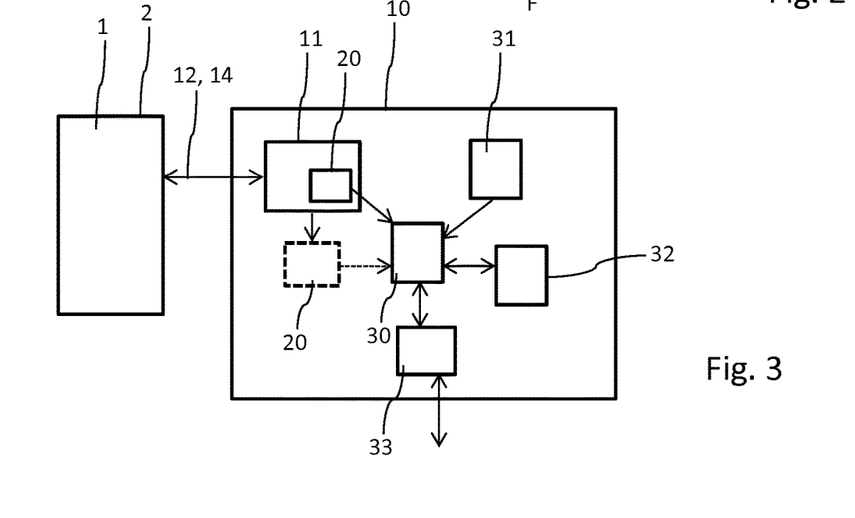
FIG. 3 is indicative of a block diagram of the supplementary device and of its components.

In FIG. 3 a schematic block diagram of the supplementary device 10 is provided. The supplementary device 10 comprises at least the body 11 and the at least one connector 12, 14. The at least one connector 12, 14 is indicated as an arrow in FIG. 3 that is configured to provide a mechanical connection to the injection device 1. The supplementary device 10 further comprises a sensor arrangement 20 which is either integrated into the body 11 or, as shown in dashed lines, which is located outside but close to the body 11. Optionally, the supplementary device 10 is further equipped with a processor 30 that is configured to receive and to process signals generated by the sensor arrangement 20. Further optionally the supplementary device 10 is equipped with a power source 31, typically in form of a battery or accumulator. The power source 31 provides electrical power and electric energy to the processor 30.

Further optionally there is provided a storage 32 that is configured to capture and to store data generated by the processor on the basis of signals obtained from the sensor arrangement 20. Alternatively, the storage 32 may be configured to store electric signals generated by the sensor arrangement 20. The processor 30 is typically configured to read and to write the storage 32. Further optionally there is provided an interface 33 in data communication with the processor 30. By means of the interface data previously stored in the storage 32 and/or electric signals provided by the sensor arrangement 20 can be transferred to an external device either wirelessly or by means of a wired data connection. The interface 33 may be implemented in accordance to commonly available wireless transmission hardware and standards, such as IEEE 802.11, Bluetooth, infrared-based communication protocols, NFC or RFID-based communication protocols, just to mention a few.

The processor 30 is typically provided with an internal clock so as to monitor the date and the time at which a dose dispensing procedure takes place.

Figure 6:
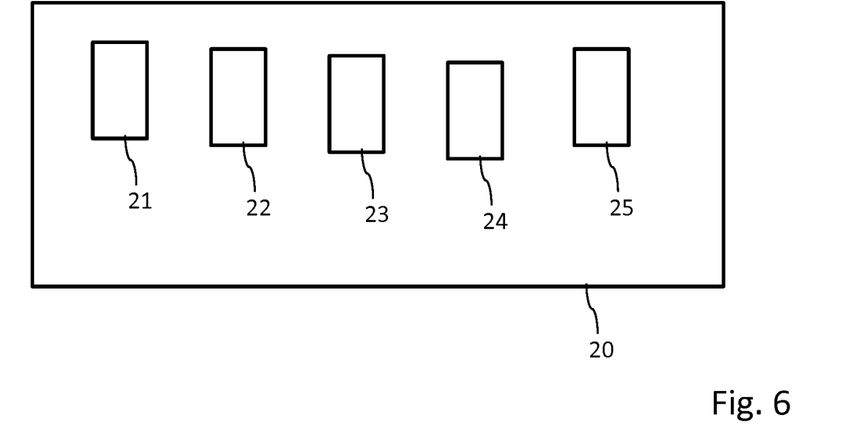
FIG. 6 shows various implementations of the sensor arrangement and of different sensors to be used with the sensor arrangement and FIG. 7 is a flowchart of the method of monitoring the operation of the injection device.

In FIG. 6 various implementations of the sensor arrangement 20 are illustrated. The sensor arrangement 20 may comprise at least one or several of a strain gauge 21, a force sensor 22, a pressure sensor 23, a switch 24 and a microphone 25. The strain gauge 21, the force sensor 22, the pressure sensor 23 and the switch 24 may be implemented as alternatives. In addition to at least one of the strain gauge 21, the force sensor 22, the pressure sensor 23 and the switch 24 the sensor arrangement 20 may further comprise the microphone 25. In one embodiment the sensor arrangement comprises at least two sensors, namely a microphone 25 and one of a strain gauge 21, a force sensor 22, a pressure sensor 23 and a switch 24.

The microphone 25 is particularly configured to detect audible click sounds generated by the click sound generator 64 at least during dose dispensing and optionally also during setting of a dose. The force sensor 22 and/or the pressure sensor 23 may comprise at least one piezoelectric element, e.g. a piezoelectric layer that is configured to generate an electric signal in response to a mechanical load. The strain gauge 21 may be integrated or implemented inside or at the body 11 and/or at the connector 12, 14. By means of the strain gauge 21 an intrinsic mechanical load acting on the body 11 may be directly monitored.

Figure 4:
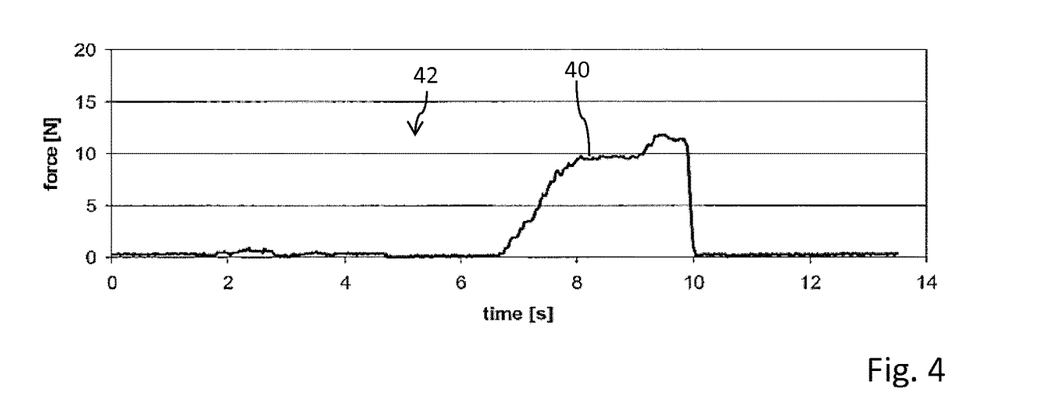
FIG. 4 is a diagram showing a signal output of the sensor arrangement over time during dose setting and dose dispensing.
Figure 5:
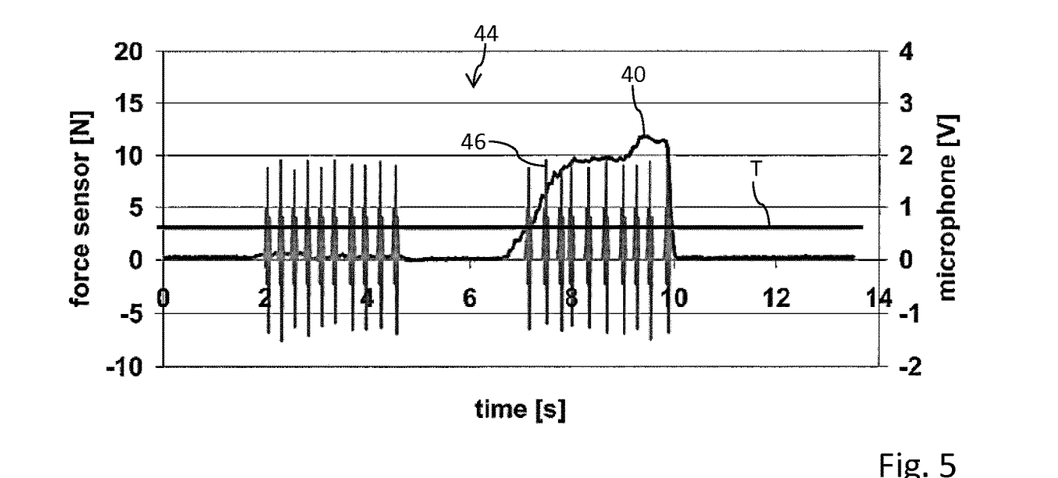
FIG. 5 is a diagram in accordance to FIG. 4 illustrating a longitudinal force component over time together with a further diagram indicative of acoustic signals recorded and captured by a microphone.

In FIGS. 4 and 5 the signal 40 of the sensor arrangement 20 is printed over time measured in seconds. The signal 40 is indicative of the magnitude of the measured longitudinal force component F in Newton. As it is apparent from FIG. 4 after 2 seconds a force is detectable with a rather low magnitude, e.g. below 1 Newton. In the time interval between 2 seconds and 5 seconds the injection device 1 is subject to a dose setting procedure. During the dose setting procedure the interconnection of body 11 and housing 2 is not subject to a longitudinal force acting therebetween. After about 7 seconds a dispensing procedure starts. As indicated in the diagram 42 of FIG. 4, the measured force rises up to a level of about 10 Newton. At about 9 seconds the force level even rises up to about 11 or 12 Newton.

Between 7 and 10 seconds the pressure or force level applied to the dose button 5 is rather constant. It is a clear indication, that a rather constant dispensing pressure is applied to the dose button 5 in distal direction. The signal 40 as illustrated in FIG. 4 is directly indicative of the counter-force and hence of the longitudinal force component F detectable and quantitatively measurable by the sensor arrangement 20.

In the diagram 44 of FIG. 5 a force threshold T is illustrated in form of a horizontal line at about 3 Newton. With the present injection device 1 this threshold force T is a typical level at which a clutch of the drive mechanism 60 opens and at which a dispensing procedure will be initiated. There is further illustrated a second signal 46 that is indicative of the output of the microphone 25. As it can be seen from FIG. 5, the signal 46 of the microphone 25 exhibits various distinct and sharp peaks, each of which representing a click sound recorded by the microphone 25. Each peak in the signal 46 represents a distinct and discrete size of a dose. For instance, any peak or any click is indicative of a dosing step of 1 or 2 international units (IU) of insulin.

In order to measure a size of a dose actually dispensed by the manually operable injection device 1 the processor 30 of the supplementary device may be programmed in such a way, that only those signals 46 that occur at a time where the signal 44 is above the threshold T are counted in order to calculate the size of a dose actually dispensed. In the time interval between 2 and 5 seconds the signal 44 indicative of the longitudinal force component F is rather low and is below the given threshold T. The click sounds and hence the peaks of the signal 46 arising in the time interval between 2 and 5 seconds are considered to be irrelevant for the measuring or determination of the size of the dose. Only peaks of the signal 46 that coincide with the rising signal 44 and those click noises that are generated between 7 and 10 seconds and that coincide with a longitudinal force component above the given threshold T are counted and evaluated. Counting of these click noises immediately leads to the size of the dose actually dispensed.

So the at least one of a strain gauge 21, a force sensor 22, a pressure sensor 23 and a switch 24 may act as an activation switch for recording or for processing signals obtained from the microphone 25.

FIGS. 1 and 2 show a kit 100 that comprises the injection device 1 and the supplementary device 10, which is actually attached thereto. Contrary to the illustrated embodiment it is also conceivable, that the supplementary device 10 and the injection device 1 of the kit 100 are provided in a detached configuration so that the end user will have to attach the supplementary device 10 to the injection device 1. It is also conceivable, that the supplementary device 10 is commercially distributed independent of the injection device 1.

Figure 7:
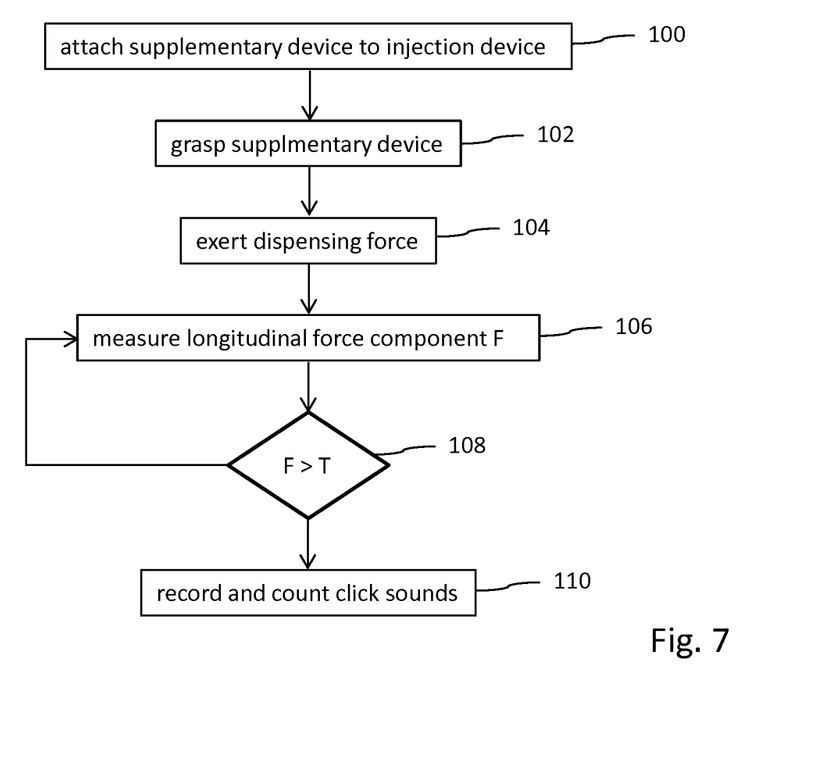

In FIG. 7 a flowchart of the method of monitoring the operation of the manually operable injection device 1 is given. In a first step 100 the supplementary device 10 as described above is attached to the housing 2 of the injection device 1. In a following step 102 the supplementary device 1 is grasped by a user with the injection device 1 attached to the supplementary device 10. Typically the user holds the kit 100 in a palm of a hand. In typical configurations the user actually uses the body 11 of the supplementary device 10 as a handhold 15. In a subsequent step 104 and assuming that a dose to be dispensed is already set, the user exerts a distally directed dispensing force D to the dose button 5 at the proximal end of the injection device 1.

In step 106 a counterforce, hence the longitudinal force component F measurable between the body 11 of the supplementary device 10 and the housing 2 of the injection device is measured. In step 108 it is determined and asserted if the measured longitudinal force component is above a predefined threshold T. If the force is below the threshold T the procedure returns to step 106. The loop of steps 106 and 108 is repeated as long as the measured pressure is below the predefined threshold T.

When it is determined in step 108 that the pressure level is above the given threshold T the method proceeds with step 110 in which a microphone 25 is activated or in which signals permanently provided by the microphone 25 are subject to further processing and analysis. Typically, in step 110 recurring or repeatedly arising click sounds generated by a click sound generator 64 of the injection device 1 are recorded and/or counted. After step 110 the procedure jumps back to step 106. As long as the applied dispensing force D and the resulting measured longitudinal force component F is above the threshold T consecutive click sounds will be recorded in step 110. In this way the size of a dose actually dispensed during application of a dispensing force onto the dose button 5 can be determined and calculated.

LIST OF REFERENCE NUMBERS 1 injection device
2 housing
3 distal end
4 proximal end
5 dose button
6 cartridge
7 piston
8 barrel
9 medicament
10 supplementary device
11 body
12 connector
14 connector
15 handhold
16 outer surface
17 inner side
18 sleeve
19 sidewall
20 sensor arrangement
21 strain gauge
22 force sensor
23 pressure sensor
24 switch
25 microphone
30 processor
31 power source
32 storage
33 interface
40 signal
42 diagram
44 diagram
46 signal
60 drive mechanism
61 piston rod
62 pressure piece
64 click sound generator
65 gear
72 protective cap
73 distal housing component
74 proximal housing component
76 sleeve
78 dose indicating window

The invention claimed is:

1. A supplementary device for a manually operable injection device, the supplementary device comprising:
a body attachable to a side surface of an elongated housing of the injection device, wherein the body is shaped to enclose at least a portion of the elongated housing and wherein the elongated housing is configured to accommodate a drive mechanism including a piston rod;
at least one connector connected to the body and connectable to the elongated housing, wherein the body is attachable to the elongated housing via the at least one connector; and
a sensor arrangement coupled to at least one of the body and the at least one connector and configured to quantitatively measure a force component acting between the elongated housing and the body in a direction parallel to a longitudinal axis of the elongated housing when the body is attached to the elongated housing.

2. The supplementary device according to claim 1, wherein the body forms a handhold with an outer surface configured to be gripped by a palm of a hand of a user.

3. The supplementary device according to claim 1, wherein the body comprises a hollow sleeve with an inner diameter that is larger than an outer diameter of the elongated housing of the injection device.

4. The supplementary device according to claim 3, wherein the at least one connector is attached to an inner side of a sidewall of the hollow sleeve.

5. The supplementary device according to claim 1, wherein the sensor arrangement is integrated into at least one of the at least one connector or the body.

6. The supplementary device according to claim 1, wherein the sensor arrangement comprises at least one of a strain gauge, a force sensor, a pressure sensor, a switch, or a microphone.

7. The supplementary device according to claim 1, further comprising a processor electrically connected to the sensor arrangement and configured to process and/or to record signals obtainable from the sensor arrangement.

8. The supplementary device according to claim 1, wherein the sensor arrangement comprises a microphone and at least one of a strain gauge, a force sensor, a pressure sensor, or a switch, and wherein the supplementary device comprises a processor configured to start processing or recording of signals from the sensor arrangement when a magnitude of the force component is above a predefined threshold.

9. A kit comprising:
a manually operable injection device comprising:

an elongated housing with a distal end and with a proximal end, wherein the elongated housing is configured to accommodate a drive mechanism including a piston rod, and a dose button located at the proximal end, wherein the dose button is depressible towards the distal end to initiate dispensing of a dose of a medicament; and a supplementary device comprising:

a body attachable to a side surface of the elongated housing of the injection device, wherein the body is shaped to enclose at least a portion of the elongated housing, at least one connector connected to the body and connectable to the elongated housing of the injection device, wherein the body is attachable to the elongated housing via the at least one connector, and a sensor arrangement coupled to at least one of the body and the at least one connector and configured to quantitatively measure a force component acting between the elongated housing and the body in a direction parallel to the elongation of the housing when the body is attached to the elongated housing.

10. The kit according to claim 5, wherein the injection device is configured to accommodate a cartridge filled with the medicament and sealed towards the proximal end with a piston displaceable inside a barrel of the cartridge and wherein the injection device further comprises:

a click sound generator configured to generate recurrent click sounds during a displacement of the piston rod towards the distal end, and wherein the piston rod of the drive mechanism is configured to operably engage with the piston for displacing the piston towards the distal end.

11. The kit according to claim 9, wherein the supplementary device is attachable or is attached to a proximal portion of the elongated housing at a predefined distance from the proximal end.

12. The kit according to claim 9, wherein the body of the supplementary device forms a handhold with an outer surface configured to be gripped by a palm of a hand of a user.

13. The kit according to claim 9, wherein the body of the supplementary device comprises a hollow sleeve with an inner diameter that is larger than an outer diameter of the housing of the injection device.

14. The kit according to claim 13, wherein the at least one connector is attached to an inner side of a sidewall of the hollow sleeve.

15. The kit according to claim 9, wherein the sensor arrangement of the supplementary device is integrated into at least one of the at least one connector or the body.

16. The kit according to claim 9, wherein the sensor arrangement of the supplementary device comprises at least one of a strain gauge, a force sensor, a pressure sensor, a switch, or a microphone.

17. A method of monitoring operation of a manually operable injection device, the method comprising:

attaching a supplementary device to a side surface of an elongated housing of the injection device, wherein the elongated housing is configured to accommodate a drive mechanism including a piston rod and wherein a body of the supplementary device is shaped to enclose at least a portion of the elongated housing, and connecting at least one connector of the supplementary device to the housing of the injection device;

grasping the supplementary device with the injection device attached thereto; and applying a force to a dose button of the injection device while the supplementary device quantitatively measures a force component acting between a body of the supplementary device and the housing in a direction parallel to the elongation of the housing.

* * * * *